(12) United States Patent
Levinson (10) Patent No.: US 6,638,296 B2
(45) Date of Patent: Oct. 28, 2003

(54) HEMOSTASIS PAD AND METHOD

(75) Inventor: Melvin Levinson, Pinecrest, FL (US)

(73) Assignee: Scion Cardiovascular, Inc., Miami, FL (US)

( * ) Notice: Subject to any disclaimer, the term of this patent is extended or adjusted under 35 U.S.C. 154(b) by 0 days.

(21) Appl. No.: 10/286,614

(22) Filed: Nov. 1, 2002

(65) Prior Publication Data

US 2003/0093075 A1 May 15, 2003

Related U.S. Application Data

(63) Continuation-in-part of application No. 10/008,052, filed on Nov. 13, 2001.

(51) Int. Cl.⁷ .............................................. A61B 17/04
(52) U.S. Cl. ........................ 606/213; 606/214; 604/180
(58) Field of Search ............................. 606/213, 214; 604/174, 180

(56) References Cited

U.S. PATENT DOCUMENTS

| | | | |
|---|---|---|---|
| 4,394,373 A | | 7/1983 | Malette et al. ................. 424/95 |
| 5,375,588 A | * | 12/1994 | Yoon ........................... 600/114 |
| 5,714,543 A | * | 2/1998 | Shah et al. .................. 525/123 |
| 5,807,341 A | * | 9/1998 | Heim .......................... 604/174 |
| 5,985,434 A | | 11/1999 | Qin et al. ................. 428/315.5 |
| 6,060,461 A | | 5/2000 | Drake |

OTHER PUBLICATIONS

Vanson Chitin Chitosan and Chitosan Derivatives Entrance; http://www.vanson.com; Jul. 27, 2001.
Chitin and Chitosan and their Medical Applications; http://www.vanson.com/pages/med/biomed.html; Jul. 27, 2001.
Properties of Chitosan; http://www.vanson.com/pages/med/Properties.html; Jul. 27, 2001.
Properties of Chitosan; http://www.vanson.com/pages/med/solution.html; Jul. 27, 2001.
Physical Forms of Chitosan and their Applications; http://www.vanson.com/pages/med/forms.html; Jul. 27, 2001.

* cited by examiner

Primary Examiner—Gary Jackson
(74) Attorney, Agent, or Firm—McDermott, Will & Emery (57) ABSTRACT

A hemostatic device comprises an adhesive bandage and a hemostatic pad. The adhesive bandage includes an adhesive backing, an absorbent pad attached to a bottom surface of the adhesive backing, and a flexible disc attached to a top surface of the adhesive backing. The adhesive backing includes a central portion and two adhesive ends extending from the central portion. The hemostatic pad is attached to a bottom surface of the absorbent pad. A hemostatic effective amount of hemostatic agent is attached to a bottom surface of the hemostatic pad. The hemostatic pad defines an aperture at an approximately central point and an elongated cut extending from the aperture. The bandage defines an associate aperture and an elongated cut above the aperture and the elongated cut of the hemostatic pad. The apertures and the cuts allow the passage of an indwelling tubular element at the puncture wound.

50 Claims, 11 Drawing Sheets

METHOD

FIG. 14

HEMOSTASIS PAD AND METHOD

REFERENCE TO RELATED APPLICATION

This application is a continuation in part of U.S. patent application Ser. No. 10/008,052, filed Nov. 13, 2001, the disclosure of which is incorporated herein by reference.

FIELD OF THE INVENTION

The present invention relates to medical devices for hemostasis, and methods of using the medical devices for hemostasis. More particularly, the present invention relates to medical devices for effecting hemostasis at a puncture wound with an indwelling tubular element extending therethrough.

BACKGROUND OF THE INVENTION

Puncture of blood vessels is a necessary stage in many of the minimally invasive approaches to diagnosis and treatment, including interventional radiology and cardiology. Therefore, a need to create hemostasis as rapidly as possible following the procedure becomes an important priority.

Various hemostatic agents, such as synthetic or natural cationic polymers, hydrogels, collagen based products, oxidized cellulose, gelatin derivatives, topical thrombin, astringents, vasoconstrictors, etc. have been and are being utilized. Most conventional devices and methods of application are designed as a pad or dressing, incorporating these hemostatic agents to the bleeding site, puncture site or wound site.

Certain medical procedures require insertion of a tubular element, such as catheter, introducer or tube in an artery or other vessel of a patient. The insertion of such tubular element makes it difficult to provide an effective hemostasis at a puncture wound because the hemostatic substances can not be applied directly and intimately under pressure to the bleeding or wound site. Also, an immediate hemostasis is often needed during surgery while a tubular element is still in the vessels of the patient or after the tubular element is removed. Therefore, what is needed is a simple, safe and effective device and method for providing more directly and intimately hemostasis to the bleeding site with an indwelling tubular element, such as catheter, introducer or tube, and allowing the tubular element to be easily removed thereafter.

SUMMARY OF THE INVENTION

The present invention provides a device and method for effecting hemostasis at a wound site with an indwelling tubular element, such as catheter, introducer or tube disposed therein.

Many hemostasis methods have been utilized or attempted, including suture-based devices, collagen plugs, pressure applying devices, and the like. The situation is complicated further by the use of anticoagulants in these procedures, which prolongs clotting times. Substances such as heparin, aspirin, coumadin, and other anticoagulants are used with regularity and affect the normal blood coagulation cascade. The use of cationic substances in flocculation and coagulation in non-medical situations such as water treatment, paper production, industrial sludge treatment, and the like has been effectively used in the past and is well documented. The method of action is by precipitating, coagulating or flocculating suspended particles which are negatively charged by virtue of using positively charged materials, which attract the oppositely charged ions.

It has been clearly demonstrated that the charge on blood cells and components (platelets, etc.) is negative. By using a positively charged biocompatible substance, it is possible to agglomerate these cells creating coagulation through a system other than by virtue of the normal clotting cascade. Innocuous polymers are positively charged (cationic substances) as the initiator of coagulation in clinical situations. Additionally, positive charges can be applied via iontophoretic methods using electrode pads and positively charged treatment sites to accomplish the same thing.

The use of a positive charge administered by either cationic substances or by iontophoretic means to quickly create a coagulation process and hemostasis until the normal clotting cascade can take over. This can occur even in the face of significant anticoagulation since the process is ionic and not effected by the anticoagulants, which operate on the normal blood cascade. This approach can be revolutionary in the after treatment of patients with minimally invasive or invasive procedures since rapid hemostasis and mobilization of the patient are desirable endpoints.

The cationic substance can be incorporated into many forms, such as woven and non-woven pads, fibers, gels, pastes, waxes, foams, sprays, liquids of varying viscosities, packings, membranes, sheets, and the like. Additionally, these forms can be incorporated and utilized with iontophoretic types of equipment that create a positive charge at the bleeding site to effect coagulation.

Utilizing colloidal chemistry for effecting coagulation ionically in suspensions or colloidal substance by providing cationic charges, has enormous value in the diagnosis and treatment of conditions such as cardiovascular disease, interventional radiological procedures, and the like. The cationic charge can be provided by a substance with a positively charged surface, or electronically by utilizing electrophoretic type equipment and electrode pads specifically designed to be disposable, conductive and sterile, designed to fit the required anatomical site. Many cationic substances are available, such as polymers, polysaccharides and starches, aluminum salts, magnesium salts, natural polymers such as chitosan, and the like.

The use of ionic charges to create hemostasis is a new and important process in the treatment of disease processes. This novel approach can be administered by applying sterile, biocompatible, positively charged materials directly in contact with the blood column, accompanied by pressure, or provided electronically by utilizing controlled direct current on the positive side with iontophoretic type approaches and specially constructed, disposable, sterile electrodes to the bleeding site According to one aspect of the present invention, a hemostatic pad defines an opening at a proximally central point of the pad. The opening is sized to allow egress of the indwelling tubular element through the pad. The pad further comprises an application surface, which contains hemostatic agent used for effecting hemostasis at the wound site associated with an indwelling tubular element. The hemostatic agent preferably is a cationic substance, such as cationic polymer, or a cationic protein. The hemostatic substance on the pad, therefore, may be applied evenly, directly and intimately around the tubular element, also providing an even application of pressure for hemostasis. It also allows the indwelling tubular element to be easily removed from the wound site through the pad. In a preferred embodiment, the opening of the pad is a slit extending from an approximate center to an edge of the pad. In another preferred embodiment, the opening is constructed as an aperture with a slit extending from the aperture to an edge of the pad.

According to another aspect of the present invention, the hemostatic pad may have a non-slip etched area on a top surface of the pad, in order to achieve more friction between the finger of a surgeon and the surface of the pad. The non-slip etched area make it easier to apply a pressure to a puncture site, and make the hemostasis more efficiently and quickly.

According to another aspect of the present invention, the hemostatic device comprises an adhesive bandage which preferably has a "Band Aid™"-like shape. The adhesive bandage includes a non-adhesive central portion and an adhesive peripheral portion, preferably two adhesive ends, extending from two opposite side of the non-adhesive central portion. The adhesive bandage defines an aperture at an approximately central point of the central portion and an elongated cut extending from the aperture to an edge of the non-adhesive central portion. The aperture is sized to allow passage of the tubular element, for example, catheter or introducer. The bandage may further include two peelable films covering the two adhesive ends of the bandage. A hemostatic effective amount of hemostatic agent or a hemostatic pad with the hemostatic agent attached thereon is attached to the non-adhesive central portion for effecting a hemostasis at a puncture wound where the adhesive bandage is applied.

According to another embodiment of the present invention, the hemostatic device includes an adhesive bandage and a hemostatic pad attached to a bottom surface of the adhesive bandage. The bandage includes an adhesive backing, an absorbent layer or pad attached to a bottom surface of the backing, and a flexible disc attached to a top surface of the backing. The adhesive backing includes a central portion and an adhesive peripheral portion extending from the central portion. In one preferred form, the disc is made of transparent plastic and is gamma radiation resistant. The disc provides a relatively hard surface for a surgeon to apply force to the hemostatic device and thereby to the puncture would, assisting the hemostasis at the puncture wound. The hemostatic pad, preferable a polymer pad, includes hemostatic agent attached thereon.

The hemostatic pad defines an aperture at an approximately central point and an elongated cut extending from the aperture. The aperture is sized to allow passage of the tubular element, for example, catheter, catheter introducer, and etc. The adhesive bandage also defines an associate aperture and elongated cut above the aperture and the elongated cut of the hemostatic pad. The aperture and the elongated cut on the adhesive bandage have a diameter and width being equal to or greater than the diameter and width of the aperture and the elongated cut on the hemostatic pad. The apertures and the elongated cuts allow passage of the tubular element extending from the puncture wound. The aperture and elongated cut on the bandage, which are bigger sized than the aperture and the elongated cut on the hemostatic pad, permit a surgeon to view the bleed site. In one preferred embodiment, the aperture and the elongated cut may form a continuous slit extending from an approximately central point of the device to an edge of the device.

According to one preferred embodiment of the present invention, the elongated cuts on the hemostatic pad and the absorbent pad of the adhesive bandage are along a common bias with respect to the central region of the adhesive backing.

In one preferred form, the adhesive peripheral portion of the bandage is shaped to two adhesive strips. The bandage may further include two peelable covers covering the adhesive side of the two adhesive strips. In another form, the device may only include one peelable cover covering the bottom surface of the whole device.

The disc may further include a rough etched area around a central point of the disc. The rough etched area helps a surgeon to apply force to the hemostatic device, thereby to the puncture wound to assist hemostasis.

The present invention also provides a method for effecting hemostasis at a puncture wound with an adhesive bandage having an opening sized to allow egress of a tubular element disposed in the puncture wound. The adhesive bandage may be applied to or removed from the wound while the tubular element is in the wound. The method includes applying pressure proximal to the puncture wound, and directing the application surface, which contains a hemostatically effective amount of cationic substances, of the adhesive bandage against the puncture wound with sufficient force to prevent fluid from exiting the puncture wound, and permitting the indwelling tubular element going through the adhesive bandage, removing the pressure on the puncture wound, and maintaining the force on the adhesive bandage against the wound for a predetermined time period, removing the force on the adhesive bandage, and remaining the adhesive bandage on the wound site. The adhesive bandage, which is adhered on the wound site, may still remain a slight pressure to the puncture wound, assisting hemostasis of the wound.

According to one aspect of the present invention, the application surface of the pad is a biopolymer of glucosamine, including but not limited to poly-N-acetylglucosamine. In some forms of the invention, the application surface is an acetate salt of a biopolymer of glucosamine.

According to further aspect of the present invention, when a tubular element is disposed in the wound, the predetermined time period is substantially proportional to the diameter of the tubular element.

The present invention provides many benefits, including reducing the time period required to stop bleeding at a puncture wound and decreasing the likelihood that a hematoma will form particularly, but not limited to, cases following removal of an introducer, a catheter or a tube from the puncture wound. These and other features and benefits of the present disclosure will become more apparent upon reading the following specification in combination with the accompanying drawing figures.

BRIEF DESCRIPTION OF THE DRAWINGS

Other features and advantages of the present invention will be apparent from the following detailed description of the drawing in which.

DETAILED DESCRIPTION OF THE PREFERRED EMBODIMENTS

The present invention is described hereinafter with specific references to the use of the present invention for sealing an incision or puncture wound with an indwelling tubular element, such as catheter, introducer or tube, through the incision or puncture wound. It is contemplated that the present invention may be used with any catheterization or other medical procedure such as laparoscopic or other minimally or less invasive surgeries wherein it is desirable to seal an incision or puncture wound in the patient to prevent the loss of the patient's body fluid therethrough.

Figure 1:
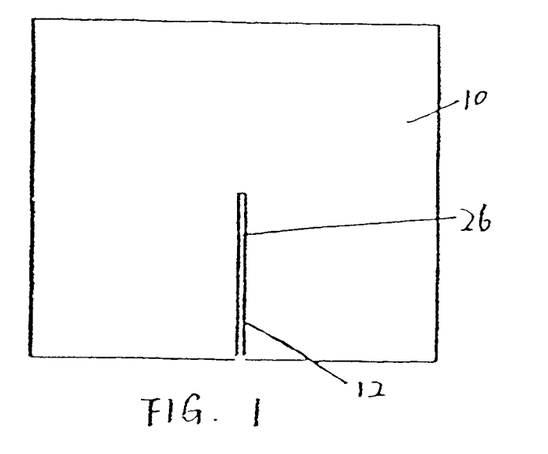
FIG. 1 is a top view of one embodiment of the present.
Figure 2:
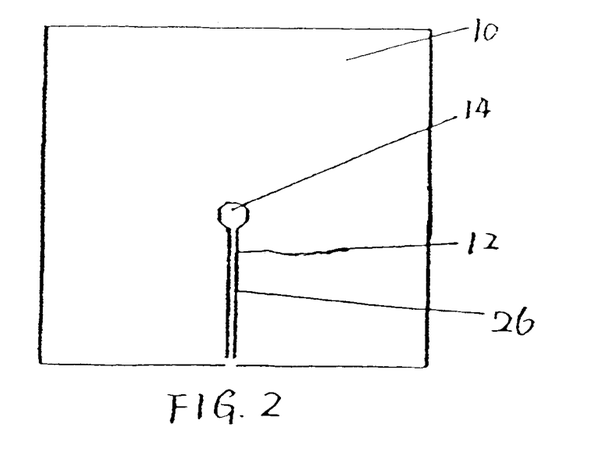
FIG. 2 is a top view of another embodiment of the present.

Referring to FIG. 1, a pad 10 defines an opening 12 through the pad 10. In a preferred embodiment, the opening is constructed as a slit or an elongated cut 26, which extends from an approximately central point to an edge of the pad 10. The slit is preferably sized to permit egress of an indwelling tubular element, such as catheter, introducer, or tube (not shown) through the pad 10. In another embodiment of the present invention, as shown in FIG. 2., the opening 12 is constructed as a generally circular aperture 14 with an elongated cut 26 extending from the aperture 14 to an edge of the pad 10. Other aperture shapes can be used.

The pad 10 further comprises an application surface (not shown), which contains hemostatic agent used for stopping the bleeding at the wound site associated with an indwelling tubular element. The hemostatic agent preferably is a cationic substance, such as cationic polymer, or a cationic protein. The hemostatic substance on the pad, therefore, may be applied evenly, directly and intimately around the tubular element, also providing an even application of pressure for hemostasis.

Figure 3:
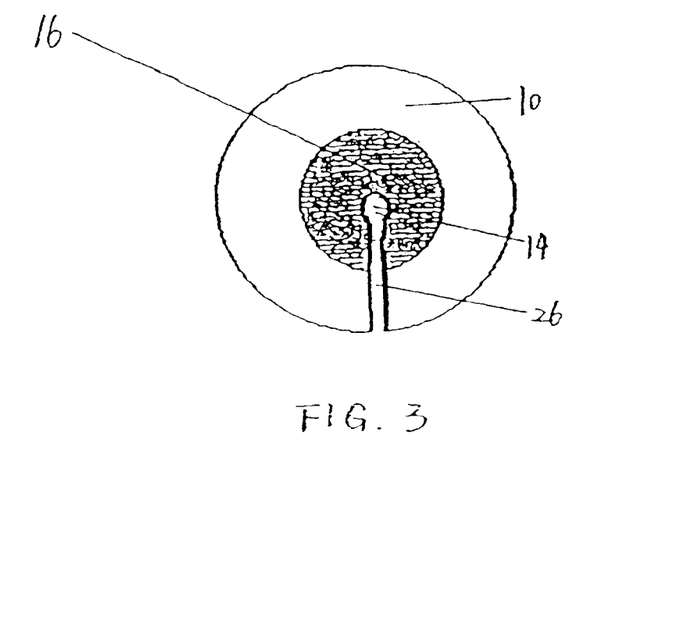
FIG. 3 is a top view of a third embodiment of the present invention.

FIG. 3 shows another embodiment of the present invention. Referring to FIG. 3, the pad 10 has a generally circular aperture 14, an elongated cut 26 extending from the aperture 14 to an edge of the pad 10, and a central non-slip etched area 16 on a top surface of pad 10 in order to provide more friction between fingers of a surgeon and the top surface of the pad. The non-slip etched area make it easier to apply a pressure to a puncture site, and make the hemostasis more efficiently and quickly.

Figure 4:
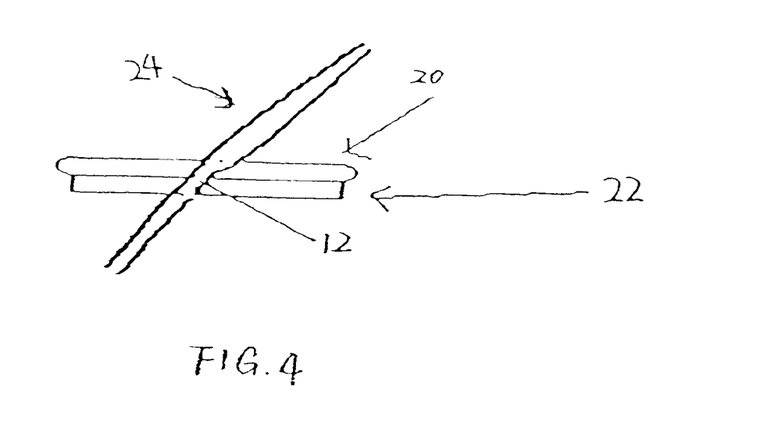
FIG. 4 is a side view of the present invention showing a catheter extending through a disc.

As shown in FIG. 4, in another preferred embodiment, a disc is used instead of the pad to effect a uniform pressure on the wound site. The disc can be rigid, semi-rigid, or flexible. The embodiment of the present invention comprises a disc 20 and a hemostatic layer 22 attached to a bottom surface of the disc. The device also has an opening 12 at an approximately central point of the disc 20. The opening is sized to permit egress of the indwelling catheter 24 or other medical equipment through the disc.

Figure 5:
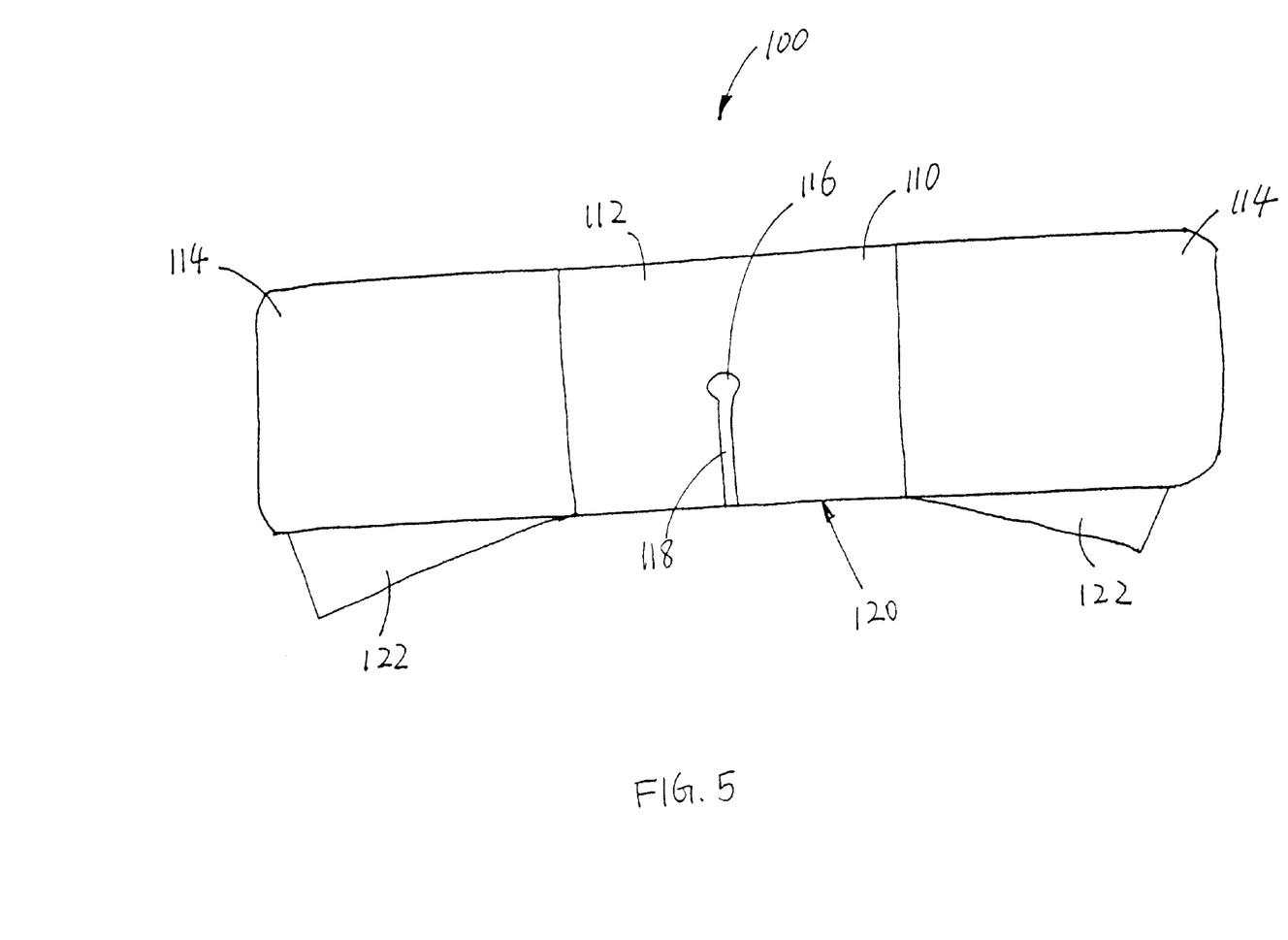
FIG. 5 is a top view of one embodiment of the present invention.
Figure 6:
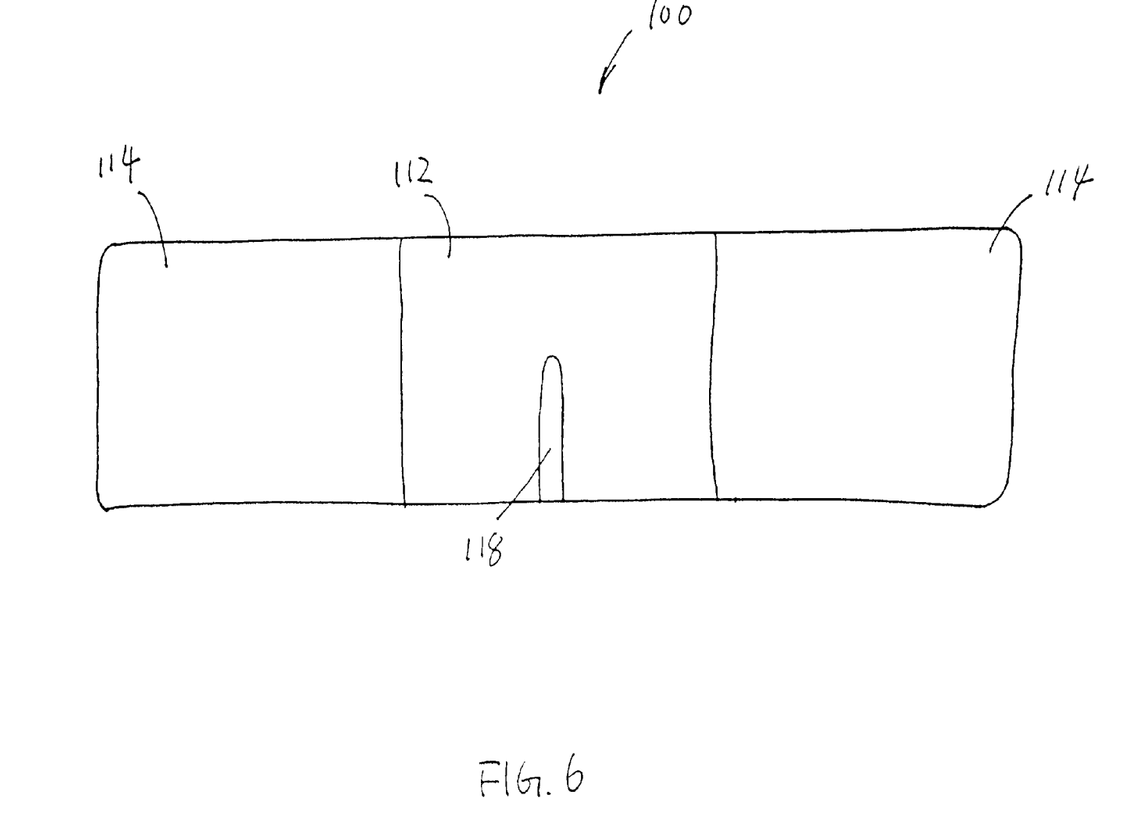
FIG. 6 is a top view of another embodiment of the present invention.

FIG. 5 shows another preferred embodiment of the present invention, in which the hemostatic device 100 comprises an adhesive bandage 110 which preferably has a "Band Aid™"-like shape. The adhesive bandage 110 includes a non-adhesive central portion 112 and an adhesive peripheral portion 114, preferably two adhesive ends, extending from two opposite side of the non-adhesive central portion. The adhesive bandage 110 defines an aperture 116 at an approximately central point of the central portion 112 and an elongated cut 118 extending from the aperture 116 to a point, preferably to an edge of the bandage 110. The aperture 116 is sized to allow passage of the tubular element, for example, catheter or introducer. In one form, as shown in FIG. 6, the bandage 110 may only defines an elongated cut or slit 118, which extends from a central point to an edge of the bandage 110. As shown in FIG. 5, the bandage 110 may further include two peelable films 122 covering the two adhesive ends 114. In FIG. 5, films 122 are shown in a partially peeled-away position. A hemostatic effective amount of hemostatic agent 120 is attached to the non-adhesive central portion 112 for effecting a hemostasis at a puncture wound where the adhesive bandage 110 is applied.

Figure 7:
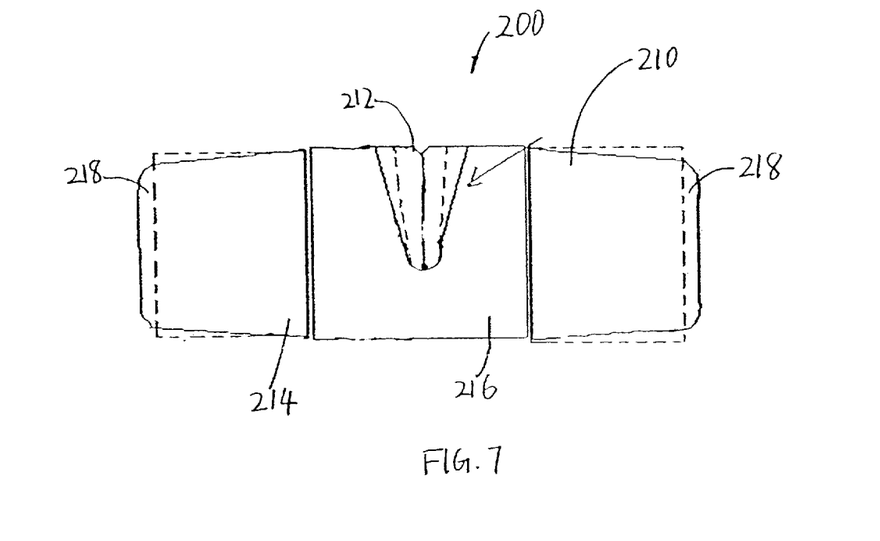
FIG. 7 is a top view of another embodiment of the present invention.
Figure 8:
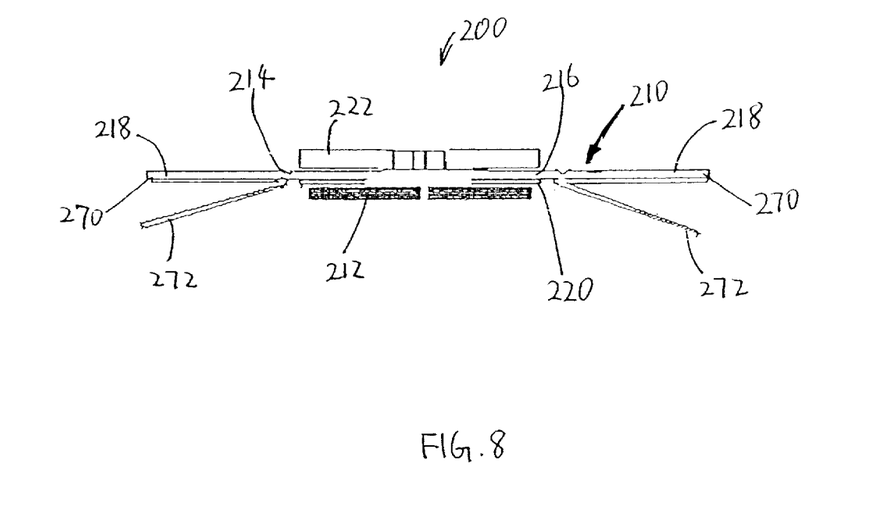
FIG. 8 is a side view of the embodiment of the present invention of FIG. 7.
Figure 9:
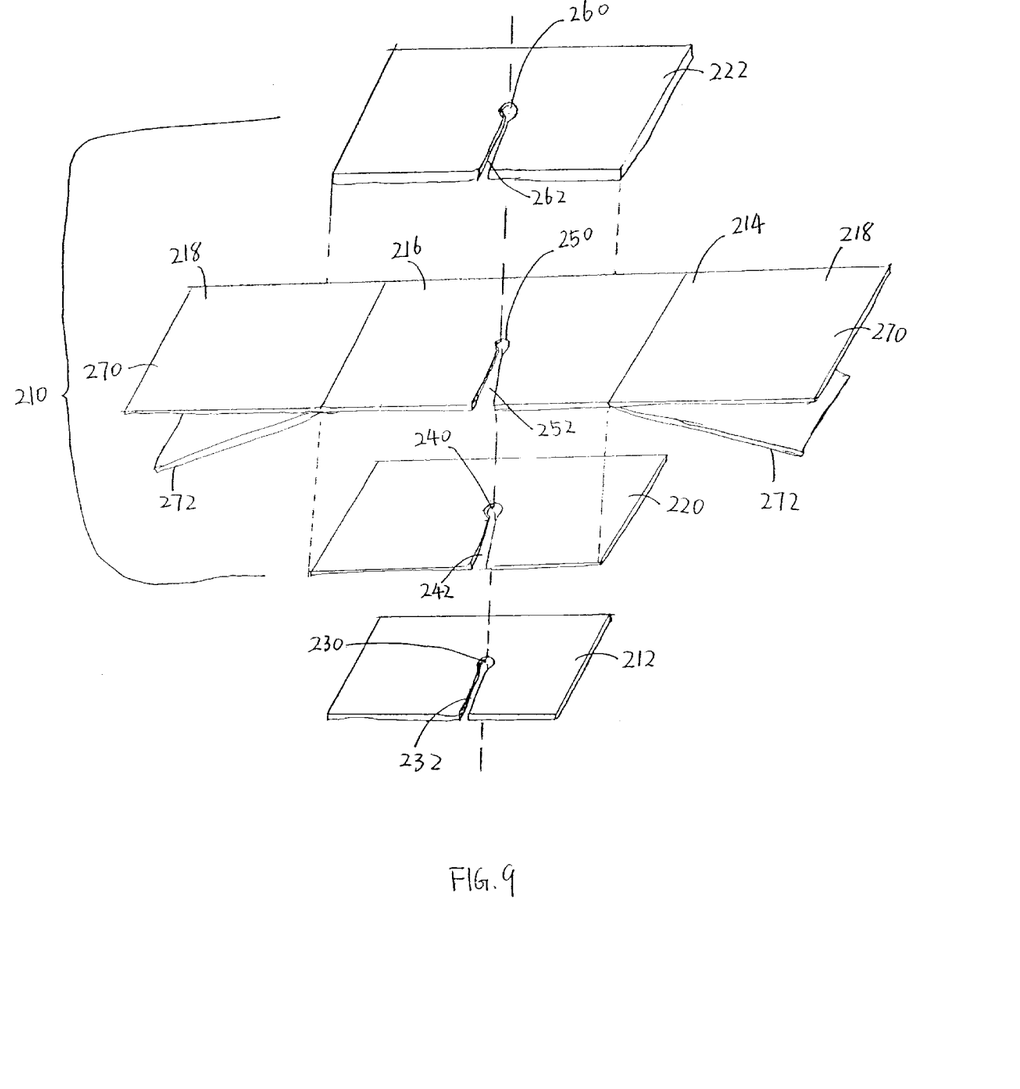
FIG. 9 is an exploded perspective view of the embodiment of the present invention of FIG. 7.

FIGS. 7, 8 and 9 illustrate another preferred embodiment of the present invention. As shown in FIG. 7, the hemostatic device 200 includes an adhesive bandage 210 and a hemostatic pad 212. FIG. 8 is side view of the hemostatic device 200 of FIG. 7. As seen in FIG. 8, the bandage 210 includes an adhesive backing 214 and an absorbent layer or pad 220, for example, gauze pad, attached to a bottom surface of a central portion 216 of the adhesive backing 214. An adhesive peripheral portion 218 extends from the central portion 216 of the adhesive backing 214. The absorbent pad 220 is useful for absorbing fluid (eg. blood) at or around the puncture wound. The bandage 210 may further include a disc 222 attached to a top surface of the central portion 216 of the adhesive backing 214. The disc 222 is flexible and preferably made of transparent plastic. In one preferred form, the disc 222 is made of a material which is gamma radiation resistant. The disc 222 provides a relatively hard surface for a surgeon to apply force to the hemostatic device and thereby to the puncture would, assisting the hemostasis at the puncture wound. The hemostatic pad 212 is attached to a bottom surface of the absorbent pad 220. The hemostatic pad 212, preferably a polymer pad, includes hemostatic agent attached on a bottom surface of the hemostatic pad 212.

FIG. 9 is an exploded perspective view of the hemostatic device 200 of FIG. 7 and FIG. 8. As shown in FIG. 9, the hemostatic pad 212 defines a generally circular aperture 230 at an approximately central point and an elongated cut 232 extending from the aperture 230. The aperture 230 is sized to allow passage of the tubular element, for example, catheter, catheter introducer, and the like. The adhesive bandage 210 also defines associated apertures and an elongated cuts on the absorbent pad 220, the adhesive backing 214, and the disc 222 above the aperture 230 and the elongated cut 232 of the hemostatic pad 212. The aperture 240 and the elongated cut 242 on the absorbent pad 220 have a diameter and width being equal to or greater than the diameter and width of the aperture 230 and the elongated cut 232 on the hemostatic pad. The aperture 250 and the elongated cut 252 on the adhesive backing 214 are sized equal to or greater than the aperture 240 and the elongated cut 242. The disc 222 also defines an associate aperture 260 and an elongated cut 262. The apertures and the cuts of the device permit egress of the indwelling tubular element. The apertures and elongated cuts on the bandage 210, which are bigger sized than the aperture and the elongated cut on the hemostatic pad, also permit a surgeon to view the bleed site from the top of the hemostatic device 200. The aperture 260 and the cut 262 may be sized smaller than the aperture 250 and the cut 252 on the backing 214, and because the disc 222 is preferably transparent, the surgeon still can view the underneath hemostatic pad and the wound site through the disc 222. In one form, the device 200 may define a single aperture and a single elongated cut throughout all the layers of the device 200. The aperture and the elongated cut of each layer have the same size with the aperture and elongated cut of other layers. In another preferred form, the elongated cuts on the bandage 210 have a wedge-like shape, permitting a better view of the underneath bleed site from the top of the bandage 210. In one preferred embodiment, the aperture and the elongated cut may form a continuous slit extending from a proximal central point of the device 200 to an edge of the device 200.

Figure 9A:
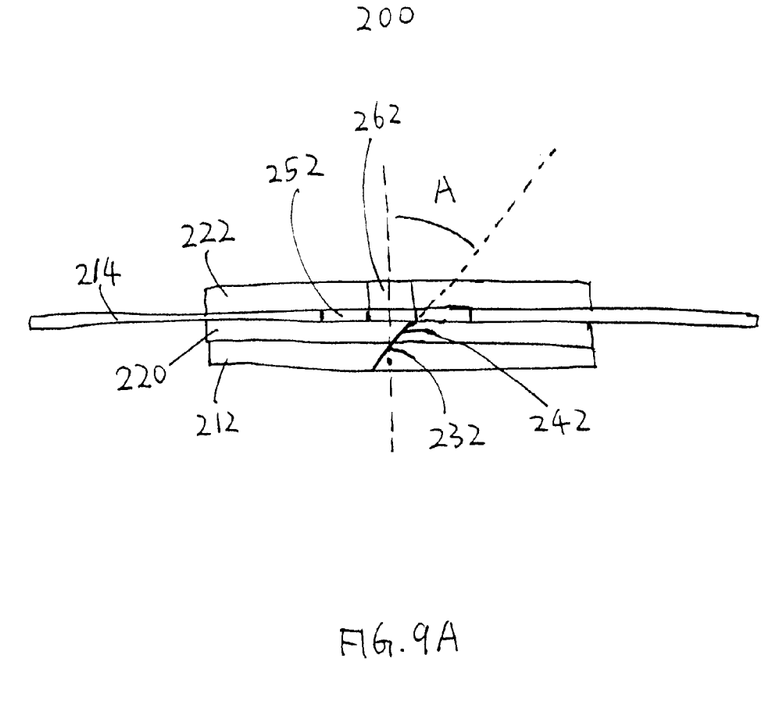
FIG. 9A is a side view of an alternative embodiment of the present invention.

FIG. 9A shows an alternative hemostatic device 200' which is similar to the device 200 shown in FIGS. 7–9. As shown in FIG. 9A, the elongated cut (232, 242) is a bias cut at an angle A with respect to the normal to the upper surface of the adhesive backing 214, preferably at 45 degrees, although other angles may be used. With that bias cut through the hemostatic pad 212 and the absorbent pad 220, the opposing bevel surfaces at the cut form a substantial closure across the cut after the flap adjacent to the cut is lifted to permit passage of a catheter (to the aperture) and then lowered again. In this embodiment, the bias cut is preferably, but not necessarily, centered with respect to and disposed across the middle third of the cut 252.

In one preferred form, the elongated bias cuts extend from the central apertures defined on the hemostatic pad and the absorbent pad. In a medical procedure, when the hemostatic device is applied to a puncture wound with an indwelling tubular element extending therefrom, the hemostatic pad and the absorbent pad with the bias cuts and the apertures thereof seal the wound around the indwelling tubular element.

Figure 9B:
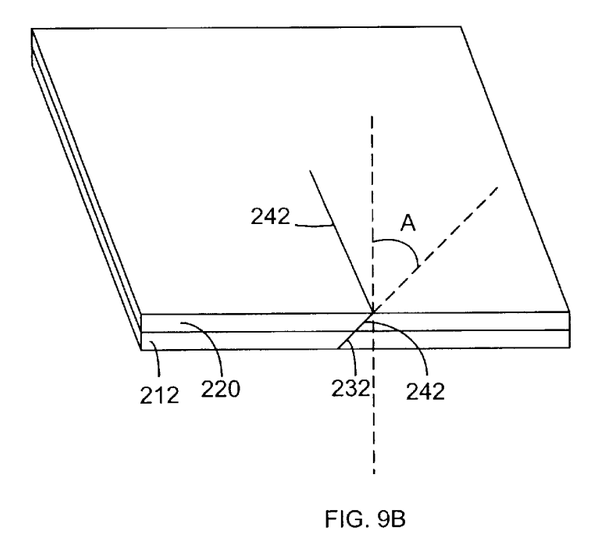
FIG. 9B is top perspective view of an absorbent pad and a hemostatic pad of one alternative embodiment of the present invention.

In another preferred form, the hemostatic device only defines an elongated cut extending from an approximately central point of the device. The two elongated cuts on the hemostatic pad and the absorbent pad are defined along a common bias with respect to the normal of the central region of the adhesive backing. FIG. 9B shows a top perspective view of the absorbent pad and the hemostatic pad of this preferred embodiment. The cuts on the adhesive backing and the disc may also be defined bias along the common bias. In a medical procedure, a surgeon can lift the flap adjacent to the cuts to allow passage of an indwelling catheter and then locate the hemostatic device on the wound with the catheter extending through the central points of the pads. After the catheter is removed, the flap close to the central points is lowered and the bevel surfaces at the cuts form a substantial closure across the cut. Thereby, the hemostatic device seals the wound to prevent the wound from exposure to the air.

Figure 10:
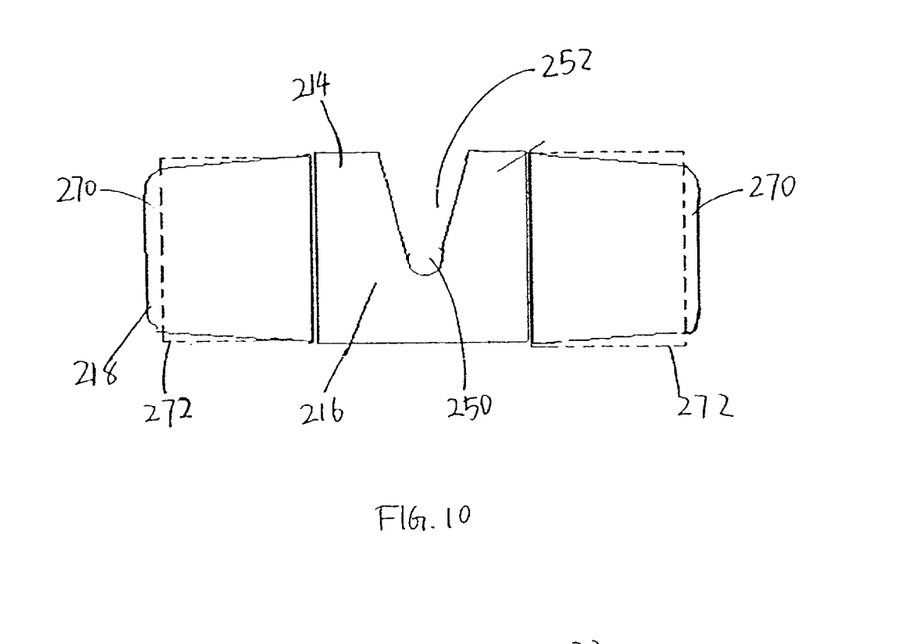
FIG. 10 is a top view of an adhesive bandage of one embodiment according to the present invention.

FIG. 10 is a top view of the adhesive backing 214 of one preferred embodiment. The aperture 250 and the elongated cut 252 form a wedge-like shaped slit extending from an approximately central point of the central portion 216 to an edge of the adhesive backing 214. As shown in the FIGS. 7, 8, 9 and 10, the adhesive peripheral portion 218 of the bandage 210 are in the form of two rectangular adhesive strips 270. The bandage 210 further includes two peelable covers 272 covering the adhesive side of the two adhesive strips 270. In a circular geometry, the bandage may include an annular adhesive periphral portion disposed about a circular central portion. During a surgery procedure, a surgeon may peel the covers 272 off, and stick the device 200 to the wound site of a patient. In another form, the device 200 may only include one peelable cover covering the entire bottom surface of the hemostatic device 200.

Figure 11:
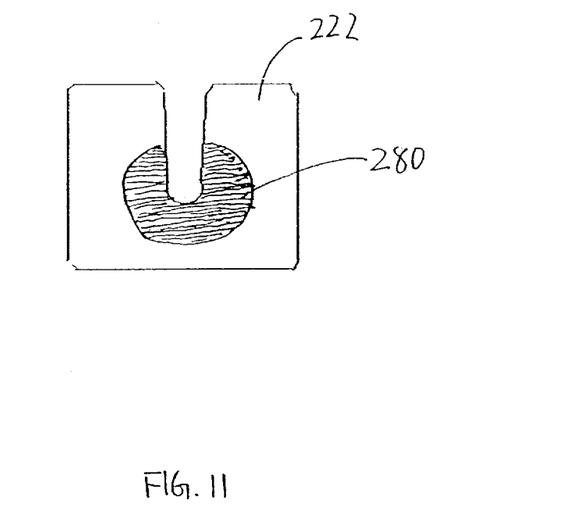
FIG. 11 is a top view of a disc of one embodiment according to the present invention.

FIG. 11 is top view of the disc 222 of the bandage 210 according to the present invention. The disc 222 is preferably flexible, transparent, and gamma radiation resistant. The disc 222 may include a rough etched area 280 around a proximal central point of the disc 222. The rough etched area 280 make it easy for a surgeon to apply force to the device 200 and thereby to the puncture wound to assist hemostasis.

Figure 12:
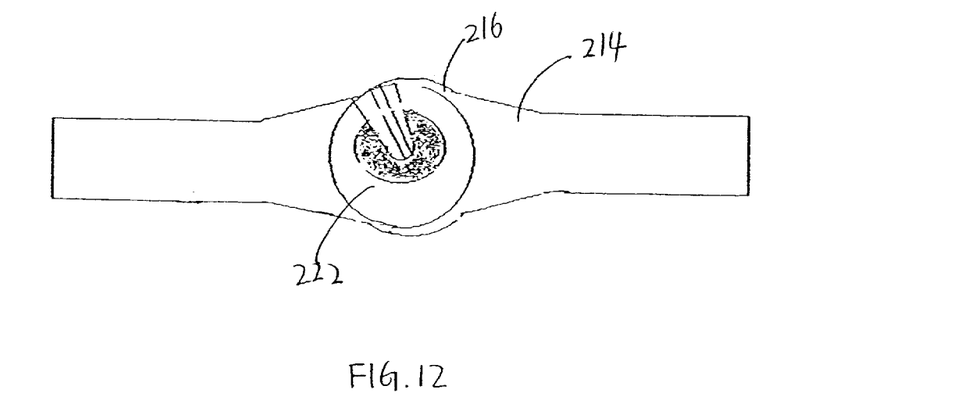
FIG. 12 is top view of another embodiment of the present invention.
Figure 13:
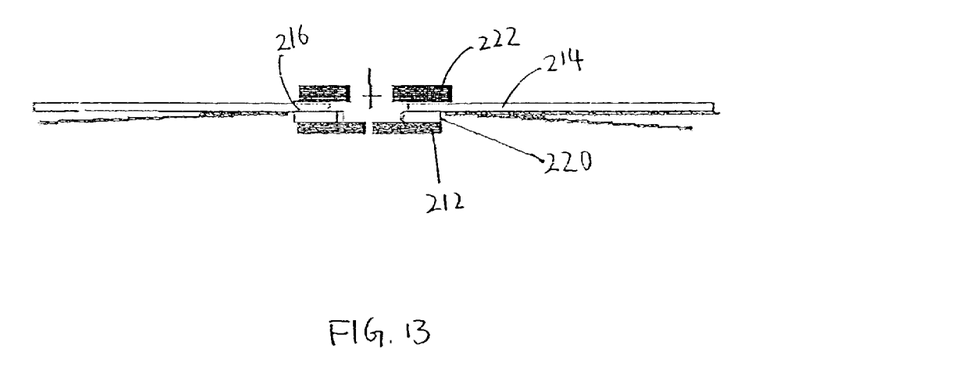
FIG. 13 is a side view of the embodiment of the present invention of FIG. 12.

FIG. 12 is a top view and FIG. 13 is a side view of another preferred embodiment of the present invention. As shown in the drawings, the absorbent pad 220, the flexible disc 222, and the central portion 216 of the backing 214 are preferably round shaped.

Figure 14:
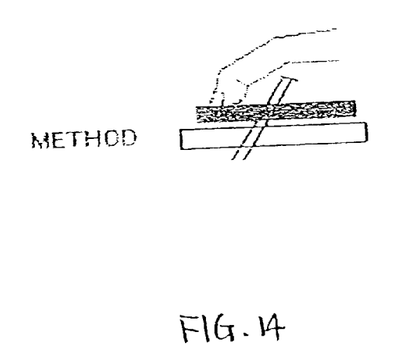
FIG. 14 shows a method of the present invention.

FIG. 14 shows a method for effecting hemostasis at a puncture wound with an indwelling tubular element extending therethrough. The method includes applying pressure proximal to the puncture wound to at least partially collapse the blood vessel (not shown), applying the hemostatic device of the present invention to the puncture wound with the indwelling tubular element passing through the aperture of the hemostatic device, directing a cationic application surface of the hemostatic device against the puncture wound with force sufficient to substantially prevent fluid from bleeding from the puncture wound, removing the pressure proximal to the puncture wound, maintaining the force on the hemostatic device against the puncture wound for at least a first predetermined time period, and removing the force on the hemostatic device. The hemostatic device is remained at the wound by sticking the adhesive strips of the hemostatic device to the skin around the wound of a patient. The hemostatic device may remain slight pressure to the wound site and that further assists hemostasis at the puncture wound.

The first predetermined time period is substantially proportional to a diameter of the tubular element, and the diameter of the resulting puncture wound as well.

In general, however, the first predetermined time period is preferably equal to about ten minutes, although other time periods can be used. In any event, the pressure may not be removed from the hemostatic device and the puncture wound until hemostasis is confirmed. Thus force may need to be maintained on the hemostatic device for longer than ten minutes. After twenty-four hours, the hemostatic device may be removed from the puncture wound.

The method of the present invention provides many benefits, including reducing the time period required to stop bleeding at a puncture wound and decreasing the likelihood that a hematoma will form after removal of a catheter from the puncture wound. The hemostatic substance therefore can be applied evenly, directly and intimately around the catheter, introducer or tube, also permitting the even application of pressure to the wound site, assisting hemostasis. It also allows for easier removal of the indwelling catheter, introducer or tube through the hemostatic device. In addition, the hemostatic pad or device may have a non-slip etched area on the top surface of the pad, in order to provide more friction between the finger of the surgeon and the surface of the pad in order to make the application of pressure to a puncture site more conveniently and allow the puncture site achieve hemostasis more efficiently.

In the above embodiment, the hemostatic agent or substance is preferably a cationic-biopolymer of glucosamine.

The cationic biopolymer of glucosamine is provided in one or more of the following forms: poly-D-glucosamine; an acetate salt of poly-N-acetylglucosamine; an acetate salt of poly-D-glucosamine; poly-N-acetylglucosamine and poly-D-glucosamine; an acetate salt of poly-N-acetylglucosamine and poly-D-glucosamine; an acetate salt of poly-N-acetylglucosamine and an acetate salt of poly-D-glucosamine; and poly-N-acetylglucosamine and an acetate salt of poly-D-glucosamine. In forms including an acetate salt, the application surface is water soluble. Acidic environments other than an acetate salt, such as lactic acid, can also be incorporated as part of the biopolymer of glucosamine.

In a preferred form, the cationic biopolymer of glucosamine is derived from chitosan, which is a collective term applied to deacetylated chitins in various stages of deacetylation and depolymerization. Chitin is the structural polymer of the exo-skeleton of arthropods and cell walls of fungi, and is composed of poly-N-Acetyl glucosamine units. These are linked by Beta 1–4 glycosidic bonds into a linear polymer containing 2,000 to 3,000 units.

The invention may be embodied in other specific forms without departing from the spirit or essential characteristics thereof. The present embodiments are therefore to be considered in all respects illustrative and not restrictive, the scope of the invention being indicated by the appended claims rather than by the foregoing description, and all changes which come within the meaning and range of equivalency of the claims are therefore intended to be embraced therein.

What is claimed is:

1. A device for effecting hemostasis at a puncture wound with an indwelling tubular element extending therethrough, said device comprising:
    an adhesive bandage, said adhesive bandage defining an aperture in a central portion thereof adapted for passage therethrough of said tubular element, and an elongated cut extending from said aperture; and
    a hemostatically effective amount of a hemostatic agent on a bottom surface of said central portion of said adhesive bandage.

2. The device of claim 1, wherein the hemostatic agent comprises a cationic biopolymer of glucosamine.

3. The device of claim 2, wherein the biopolymer of glucosamine is poly-N-acetylglucosamine.

4. The device of claim 2, wherein the biopolymer of glucosamine is poly-D-glucosamine.

5. The device of claim 2, wherein the biopolymer of glucosamine is an acetate salt of poly-N-acetylglucosamine.

6. The device of claim 2, wherein the biopolymer of glucosamine is an acetate salt of poly-D-glucosamine.

7. The device of claim 2, wherein the biopolymer of glucosamine is poly-N-acetylglucosamine and poly-D-glucosamine.

8. The device of claim 2, wherein the biopolymer of glucosamine is an acetate salt of poly-N-acetylglucosamine and poly-D-glucosamine.

9. The device of claim 2, wherein the biopolymer of glucosamine is an acetate salt of poly-N-acetylglucosamine and an acetate salt of poly-D-glucosamine.

10. The device of claim 2, wherein the biopolymer of glucosamine is poly-N-acetylglucosamine and an acetate salt of poly-D-glucosamine.

11. The device of claim 1, wherein the tubular element is a catheter.

12. The device of claim 1, wherein the tubular element is an introducer.

13. The device of claim 1, wherein the tubular element is a tube.

14. The device of claim 1, wherein said aperture and said cut form a slit.

15. The device of claim 14, wherein said slit is at a bias angle with respect to the central portion of the adhesive bandage.

16. The device of claim 1 further comprising a central non-slip etched area on a top surface of said adhesive bandage.

17. The device of claim 1, wherein said cut extends to a peripheral edge of said adhesive bandage.

18. The device of claim 1, wherein said adhesive bandage includes two adhesive ends extending from said central portion.

19. The device of claim 18 further comprising at least one peelable cover covering adhesive side of said two adhesive ends.

20. The device of claim 1, wherein said cut is at a bias angle with respect to the central portion of the adhesive bandage.

21. The device of claim 20, wherein said cut is at a bias angle of 45 degrees with respect to the central portion of the adhesive bandage.

22. A device for effecting hemostasis at a puncture wound with an indwelling tubular element extending therethrough, said device comprising:
    an bandage comprising:
        an adhesive backing having a central region;
        an absorbent pad attached to a bottom surface of the central region of the adhesive backing; and
        a hemostatic pad attached to a bottom surface of the absorbent pad, said hemostatic pad having hemostatic agent attached on a bottom surface of said hemostatic pad; and
    wherein said hemostatic pad defines a first aperture at an approximately central point of said hemostatic pad and a first elongated cut extending from said first aperture to an edge of said hemostatic pad,
    wherein said absorbent pad defines a second aperture and a second elongated cut above said first aperture and said first elongated cut,
    and wherein said adhesive backing defines a third aperture and a third elongated cut above said second aperture and said second elongated cut, said first, second and third apertures being adapted for passage therethrough of said tubular element.

23. The device of claim 22, wherein the hemostatic agent comprises a cationic biopolymer of glucosamine.

24. The device of claim 23, wherein the biopolymer of glucosamine is poly-N-acetylglucosamine.

25. The device of claim 23, wherein the biopolymer of glucosamine is poly-D-glucosamine.

26. The device of claim 23, wherein the biopolymer of glucosamine is an acetate salt of poly-N-acetylglucosamine.

27. The device of claim 23, wherein the biopolymer of glucosamine is an acetate salt of poly-D-glucosamine.

28. The device of claim 23, wherein the biopolymer of glucosamine is poly-N-acetylglucosamine and poly-D-glucosamine.

29. The device of claim 23, wherein the biopolymer of glucosamine is an acetate salt of poly-N-acetylglucosamine and poly-D-glucosamine.

30. The device of claim 23, wherein the biopolymer of glucosamine is an acetate salt of poly-N-acetylglucosamine and an acetate salt of poly-D-glucosamine.

31. The device of claim 23, wherein the biopolymer of glucosamine is poly-N-acetylglucosamine and an acetate salt of poly-D-glucosamine.

32. The device of claim 22, wherein the tubular element is a catheter.

33. The device of claim 22, wherein the tubular element is an introducer.

34. The device of claim 22, wherein the tubular element is a tube.

35. The device of claim 22, wherein the bandage further comprises a disc attached to a top surface of said adhesive backing, said disc defining a fourth aperture and a fourth elongated cut above said third aperture and third elongated cut of said adhesive backing.

36. The device of claim 35 further comprising a central non-slip etched area on a top surface of said disc.

37. The device of claim 35, wherein the disc is made of plastic.

38. The device of claim 37, wherein the disc is transparent.

39. The device of claim 37, wherein the plastic is gamma radiation resistant.

40. The device of claim 22 further comprising a central non-slip etched area on a top surface of said bandage.

41. The device of claim 22, wherein the adhesive backing includes two adhesive ends.

42. The device of claim 41 further comprising at least one peelable cover covering the adhesive side of the two adhesive ends.

43. The device of claim 22, wherein the third elongated cut of said adhesive backing has a substantially wedge shape.

44. The device of claim 22, wherein said first elongated cut and said second elongated cut are along a common bias with respect to the central region of the adhesive backing.

45. The device of claim 44, wherein said common bias is at an angle of 45 degrees with the central region of the adhesive backing.

46. A device for effecting hemostasis at a puncture wound with an indwelling tubular element extending therethrough, said device comprising:
   an bandage comprising:
      a adhesive backing having a central region;
      an absorbent pad attached to a bottom surface of the central region of the adhesive backing;
      a hemostatic pad attached to a bottom surface of the absorbent pad; and
   wherein said hemostatic pad defines a first elongated cut extending from an approximately central point of the hemostatic pad,
   wherein said absorbent pad defines a second elongated cut above said first elongated cut of the hemostatic pad, and
   wherein said adhesive backing defines a third elongated cut above said second elongated cut of said absorbent pad, said first, second and third elongated cut being adapted for passage therethrough of said tubular element.

47. The device of claim 46 further comprising a disc attached to a top surface of said bandage, said disc defining a fourth elongated cut above said third elongated cut of the adhesive backing to allow the tubular element to pass through said device.

48. The device of claim 46, wherein said first elongated cut and said second elongated cut are along a common bias with respect to the central region of the adhesive backing.

49. The device of claim 48, wherein said common bias is at an angle of 45 degrees with respect to the central region of the adhesive backing.

50. A method for effecting hemostasis at a puncture wound with an indwelling tubular element extending therethrough, said method comprising:
   A) applying pressure proximal to the puncture wound in order to at least partially prevent blood from exiting the puncture wound;
   B) providing an adhesive bandage having an application surface bearing a hemostatically effective amount of a hemostatic agent thereon, and wherein said adhesive bandage defines an aperture therethough to permit egress of said indwelling tubular element through said adhesive bandage, and includes a cut extending from said aperture to a peripheral point of said adhesive bandage;
   C) directing said adhesive bandage toward the wound while guiding said cut about said tubular element until said tubular element is resident in said aperture and said application surface is disposed about and to the wound, wherein said adhesive bandage is adhered to the wound;
   D) directing force against said adhesive bandage sufficient to substantially prevent blood from exiting the puncture wound;
   E) removing the pressure proximal to the puncture wound;
   F) maintaining the force on said adhesive bandage against the puncture wound for at least a first predetermined time period; and
   G) removing the force on said adhesive bandage.

* * * * *